(12) United States Patent  
Faryniarz et al.

(10) Patent No.: US 7,927,614 B2
(45) Date of Patent: Apr. 19, 2011

(54) ANTI-AGING TREATMENT USING COPPER AND ZINC COMPOSITIONS

(75) Inventors: Joseph R. Faryniarz, Middlebury, CT (US); Jose E. Ramirez, Trumbull, CT (US)

(73) Assignee: JR Chem, LLC, Key West, FL (US)

( * ) Notice: Subject to any disclaimer, the term of this patent is extended or adjusted under 35 U.S.C. 154(b) by 0 days.

(21) Appl. No.: 11/452,642

(22) Filed: Jun. 14, 2006

(65) Prior Publication Data

US 2007/0184017 A1    Aug. 9, 2007

Related U.S. Application Data

(60) Provisional application No. 60/764,967, filed on Feb. 3, 2006.

(51) Int. Cl.
*A61K 8/02* (2006.01)
*A61K 33/30* (2006.01)
*A61K 33/34* (2006.01)

(52) U.S. Cl. ............ 424/401; 424/400; 424/67; 424/69; 424/617; 424/630; 424/641; 424/642

(58) Field of Classification Search ........................ None
See application file for complete search history.

(56) References Cited

U.S. PATENT DOCUMENTS

| | | |
|---|---|---|
| 46,494 A | 2/1865 | Pike |
| 51,868 A | 1/1866 | Schuster |
| 55,889 A | 6/1866 | Noll |
| 81,008 A | 8/1868 | Roemheld |
| 81,711 A | 9/1868 | Van Wagenen |
| 87,343 A | 3/1869 | Johnson |
| 88,973 A | 4/1869 | McDowell |
| 92,065 A | 6/1869 | Lighthall |
| 93,300 A | 8/1869 | Hall et al. |
| 116,875 A | 7/1871 | Shannon |
| 124,751 A | 3/1872 | Lauer |
| 127,925 A | 6/1872 | Roskopf |
| 128,385 A | 6/1872 | Goffinet |
| 145,749 A | 6/1873 | Pawlewski et al. |
| 140,768 A | 7/1873 | Fisher |
| 143,133 A | 9/1873 | Fehr |

(Continued)

FOREIGN PATENT DOCUMENTS

JP     2001039809 A  *  2/2001

(Continued)

OTHER PUBLICATIONS

Rodríguez-Martín Y., "Alternating cationic-anionic layers in the $[MII(H_2O)_6][Cu^{II}(mal)_2(H_2O)]$ complexes linked through hydrogen bonds (M=Mn, Co, Ni, Cu and Zn; $H_2$mal=Malonic acid)", *CrystEngComm*, 2002, vol. 4, No. 107, 631.

(Continued)

*Primary Examiner* — Lakshmi S Channavajjala
(74) *Attorney, Agent, or Firm* — Carter, DeLuca, Farrell & Schmidt, LLP

(57) ABSTRACT

Composition and methods for alleviating or eliminating age related skin conditions by providing an effective amount of one or more copper, zinc and copper-zinc compositions are disclosed. Treatment is accomplished through the use of topical compositions containing one or more copper or zinc salts and/or copper-zinc compounds or complexes, particularly copper-zinc malonate active ingredient.

23 Claims, 5 Drawing Sheets

U.S. PATENT DOCUMENTS

| | | | |
|---|---|---|---|
| 149,857 A | 1/1874 | Halpen | |
| 173,607 A | 6/1875 | Fehr | |
| 171,875 A | 1/1876 | Sievers | |
| 209,331 A | 6/1878 | Daniel | |
| 229,014 A | 6/1880 | Sharetts | |
| 232,807 A | 10/1880 | Dennett | |
| 238,015 A | 2/1881 | Yater | |
| 264,783 A | 9/1882 | Squier | |
| 277,221 A | 5/1883 | Buse | |
| 284,335 A | 9/1883 | Scott | |
| 318,468 A | 5/1885 | Haley | |
| 320,836 A | 6/1885 | Bisaillon | |
| 411,657 A | 9/1889 | Grosbety | |
| 415,208 A | 11/1889 | Johnson | |
| 430,048 A | 6/1890 | Wainwright | |
| 432,611 A | 7/1890 | Hall | |
| 627,296 A | 6/1899 | Camnitzer | |
| 928,539 A | 7/1909 | Pucciarelli | |
| 944,738 A | 12/1909 | Loose | |
| 992,937 A | 5/1911 | Brodbeck et al. | |
| 1,059,841 A | 4/1913 | Crookes | |
| 1,086,900 A | 2/1914 | David | |
| 1,332,190 A | 2/1920 | Hull | |
| 1,411,577 A | 4/1922 | Mullins et al. | |
| 1,488,097 A | 3/1924 | Creger | |
| 1,584,173 A | 5/1926 | Holzapfel | |
| 1,593,485 A | 7/1926 | Crosnier | |
| 1,627,963 A | 5/1927 | Fuller | |
| 1,809,082 A | 6/1931 | Urkov et al. | |
| 1,908,176 A | 5/1933 | Osterberg | |
| 1,947,568 A | 2/1934 | Noonan | |
| 1,949,797 A | 3/1934 | Kaufmann | |
| 1,982,148 A | 11/1934 | Zimbron, Jr. | |
| 2,002,829 A | 5/1935 | Osterberg | |
| 2,054,989 A | 9/1936 | Moore | |
| 2,087,162 A | 7/1937 | Moore | |
| 2,095,092 A | 10/1937 | Barton | |
| 2,114,490 A | 4/1938 | Harris | |
| 2,129,836 A | 9/1938 | Goodman | |
| 2,153,653 A | 4/1939 | Stux | |
| 2,194,218 A | 3/1940 | Thurstan | |
| 2,223,142 A | 11/1940 | Weirich | |
| 2,241,331 A | 5/1941 | Shelton | |
| 2,254,636 A | 9/1941 | Vangunten | |
| 2,267,739 A | 12/1941 | Kemppe | |
| 2,289,125 A | 7/1942 | Keil | |
| 2,299,604 A | 10/1942 | Weirich | |
| 2,344,830 A | 3/1944 | Mohs | |
| 2,361,161 A | 10/1944 | Anderson | |
| 2,370,561 A | 2/1945 | Mecca | |
| 2,372,807 A | 4/1945 | Brown | |
| 2,420,271 A | 5/1947 | Travis et al. | |
| 2,420,389 A | 5/1947 | Travis et al. | |
| 2,469,228 A | 5/1949 | Gertler | |
| 2,527,686 A | 10/1950 | Sandberg | |
| 2,556,567 A | 6/1951 | Wright | |
| 2,602,039 A | 8/1952 | Wershaw | |
| 2,649,398 A | 8/1953 | Wright et al. | |
| 2,652,355 A | 9/1953 | Ercoli et al. | |
| 2,673,364 A | 3/1954 | Diveley | |
| 2,703,777 A | 3/1955 | Feinstein et al. | |
| 2,736,681 A | 2/1956 | Tishler | |
| 2,748,781 A | 6/1956 | Collat | |
| 2,838,440 A | 6/1958 | Thurmon | |
| 2,843,522 A | 7/1958 | Mahon | |
| 2,846,322 A | 8/1958 | Buchalter | |
| 2,870,150 A | 1/1959 | Wright et al. | |
| 2,870,151 A | 1/1959 | Wright et al. | |
| 2,872,372 A | 2/1959 | Hull | |
| 2,991,224 A | 7/1961 | Bell | |
| 3,013,883 A | 12/1961 | Welcker et al. | |
| 3,033,755 A | 5/1962 | Jacobi | |
| 3,035,988 A | 5/1962 | Cohen | |
| 3,084,105 A | 4/1963 | Slodki | |
| 3,137,622 A | 6/1964 | Mueller et al. | |
| 3,146,168 A | 8/1964 | Battista | |
| 3,164,523 A | 1/1965 | Fox et al. | |
| 3,184,376 A | 5/1965 | Degoli | |
| 3,210,248 A | 10/1965 | Feldmann et al. | |
| 3,215,599 A | 11/1965 | Thau et al. | |
| 3,255,079 A | 6/1966 | Schroeder et al. | |
| 3,290,218 A | 12/1966 | Joachim de Jong | |
| 3,317,372 A | 5/1967 | Hart | |
| 3,366,114 A | 1/1968 | Kanter | |
| 3,590,123 A | 6/1971 | Melloh et al. | |
| 3,749,772 A | 7/1973 | Cardarelli et al. | |
| 3,821,370 A | 6/1974 | Tenta | |
| 3,821,371 A | 6/1974 | Battista | |
| 3,826,845 A | 7/1974 | Suyama et al. | |
| 3,856,941 A | 12/1974 | Turner | |
| 3,896,238 A | 7/1975 | Smith | |
| 3,903,268 A | 9/1975 | Balassa | |
| 3,949,072 A | 4/1976 | Tenta | |
| 4,048,300 A | 9/1977 | Tomlinson et al. | |
| 4,100,269 A | 7/1978 | Pader | |
| 4,138,477 A | 2/1979 | Gaffar | |
| 4,146,607 A | 3/1979 | Ritchey | |
| 4,154,911 A * | 5/1979 | Bak et al. | 524/161 |
| 4,160,821 A | 7/1979 | Sipos | |
| 4,161,526 A | 7/1979 | Gorman | |
| 4,166,108 A | 8/1979 | Brown et al. | |
| 4,226,851 A | 10/1980 | Sompayrac | |
| 4,226,889 A | 10/1980 | Yuhas | |
| 4,229,430 A | 10/1980 | Fahim et al. | |
| 4,229,437 A | 10/1980 | Likens et al. | |
| 4,255,418 A | 3/1981 | Bailey | |
| 4,273,763 A | 6/1981 | Horrobin | |
| 4,285,967 A | 8/1981 | Gubernick et al. | |
| 4,291,025 A | 9/1981 | Pellico | |
| 4,298,601 A | 11/1981 | Howard | |
| 4,302,447 A | 11/1981 | Horrobin | |
| 4,305,842 A * | 12/1981 | Asakawa et al. | 502/202 |
| 4,309,989 A | 1/1982 | Fahim | |
| 4,310,516 A | 1/1982 | Chang et al. | |
| 4,315,916 A | 2/1982 | Likens et al. | |
| 4,322,400 A | 3/1982 | Yuhas | |
| 4,330,527 A | 5/1982 | Arima et al. | |
| 4,331,653 A | 5/1982 | Brown et al. | |
| 4,335,110 A | 6/1982 | Collins | |
| 4,349,536 A | 9/1982 | Hausler | |
| 4,372,296 A | 2/1983 | Fahim | |
| 4,375,968 A | 3/1983 | Manhart | |
| 4,376,115 A | 3/1983 | McCrorey | |
| 4,395,398 A | 7/1983 | Yamamoto | |
| 4,406,881 A | 9/1983 | Ladanyi | |
| 4,428,933 A | 1/1984 | King | |
| 4,430,324 A | 2/1984 | Viccaro | |
| 4,444,755 A | 4/1984 | Horrobin | |
| 4,465,666 A | 8/1984 | Lukas et al. | |
| 4,469,684 A | 9/1984 | Huggins et al. | |
| 4,477,439 A | 10/1984 | D'Aelio | |
| 4,486,488 A | 12/1984 | Pietsch et al. | |
| 4,503,037 A | 3/1985 | Szijjarto et al. | |
| 4,512,978 A | 4/1985 | Inwood | |
| 4,515,779 A | 5/1985 | Elliott | |
| 4,522,806 A | 6/1985 | Muhlemann et al. | |
| 4,568,540 A | 2/1986 | Asano et al. | |
| 4,604,234 A | 8/1986 | Fujii et al. | |
| 4,606,920 A | 8/1986 | Walter | |
| 4,647,452 A | 3/1987 | Ritchey et al. | |
| 4,654,213 A | 3/1987 | Ramirez et al. | |
| 4,661,354 A | 4/1987 | Finnerty | |
| 4,665,054 A | 5/1987 | Pickart | |
| 4,678,664 A | 7/1987 | Schmolka | |
| 4,683,133 A | 7/1987 | Southard | |
| 4,713,242 A | 12/1987 | Trenzeluk | |
| 4,760,051 A | 7/1988 | Pickart | |
| 4,762,715 A | 8/1988 | Lukas et al. | |
| 4,767,753 A | 8/1988 | Pickart | |
| 4,810,693 A | 3/1989 | Pickart | |
| 4,816,254 A | 3/1989 | Moss | |
| 4,847,083 A | 7/1989 | Clark | |
| 4,849,211 A | 7/1989 | Schrauzer | |
| 4,855,138 A | 8/1989 | Trenzeluk | |
| 4,863,897 A * | 9/1989 | Dede et al. | 514/6 |
| 4,863,987 A | 9/1989 | Hoshino et al. | |
| 4,874,361 A | 10/1989 | Obagi | |

| | | | | | | |
|---|---|---|---|---|---|---|
| 4,877,770 A | 10/1989 | Pickart | | 5,827,884 A | 10/1998 | Obagi et al. |
| 4,895,727 A | 1/1990 | Allen | | 5,837,270 A | 11/1998 | Burgess |
| 4,911,932 A | 3/1990 | Clum et al. | | 5,855,873 A | 1/1999 | Yam |
| 4,937,230 A | 6/1990 | Pickart | | 5,858,335 A | 1/1999 | Lucas et al. |
| 4,938,969 A | 7/1990 | Schinitsky et al. | | 5,858,371 A | 1/1999 | Singh et al. |
| 4,956,354 A | 9/1990 | Gutierrez | | 5,858,993 A | 1/1999 | Pickart |
| RE33,512 E | 1/1991 | Ramirez et al. | | 5,861,143 A | 1/1999 | Peterson et al. |
| 4,992,259 A | 2/1991 | Schiraldi et al. | | 5,861,144 A | 1/1999 | Peterson et al. |
| 5,000,944 A | 3/1991 | Prencipe et al. | | 5,861,145 A | 1/1999 | Lucas et al. |
| 5,023,237 A | 6/1991 | Pickart | | 5,861,146 A | 1/1999 | Peterson et al. |
| 5,059,588 A | 10/1991 | Pickart | | 5,861,147 A | 1/1999 | Dodd et al. |
| 5,075,469 A | 12/1991 | Chevion | | 5,871,718 A | 2/1999 | Lucas et al. |
| 5,079,010 A | 1/1992 | Natterer | | 5,871,719 A | 2/1999 | Lucas et al. |
| 5,091,171 A | 2/1992 | Yu et al. | | 5,874,067 A | 2/1999 | Lucas et al. |
| 5,091,193 A | 2/1992 | Enjolras et al. | | 5,874,070 A | 2/1999 | Trinh et al. |
| 5,093,099 A | 3/1992 | Haishi et al. | | 5,879,666 A | 3/1999 | Lucas et al. |
| 5,104,644 A | 4/1992 | Douglas | | 5,882,638 A | 3/1999 | Dodd et al. |
| 5,118,665 A | 6/1992 | Pickart | | 5,886,184 A | 3/1999 | Dolling et al. |
| 5,120,831 A | 6/1992 | Pickart | | 5,888,515 A | 3/1999 | Albert et al. |
| 5,135,913 A | 8/1992 | Pickart | | 5,888,522 A | 3/1999 | Pickart |
| 5,145,838 A | 9/1992 | Pickart | | 5,897,854 A | 4/1999 | Lucas et al. |
| 5,154,932 A | 10/1992 | Burba, III et al. | | 5,897,855 A | 4/1999 | Trinh et al. |
| 5,164,367 A | 11/1992 | Pickart | | 5,897,856 A * | 4/1999 | Trinh et al. |
| 5,165,914 A | 11/1992 | Vlock | | 5,904,921 A * | 5/1999 | Bresson-Rival et al. ..... 424/94.3 |
| 5,166,176 A | 11/1992 | Obagi et al. | | 5,911,976 A | 6/1999 | Trinh et al. |
| 5,174,990 A | 12/1992 | Douglas | | 5,928,631 A | 7/1999 | Lucas et al. |
| 5,177,061 A | 1/1993 | Pickart | | 5,928,658 A | 7/1999 | Kishida et al. |
| 5,209,932 A | 5/1993 | Nichols | | 5,928,659 A | 7/1999 | Moy |
| 5,214,032 A | 5/1993 | Pickart | | 5,935,608 A | 8/1999 | Fujikawa et al. |
| 5,227,156 A | 7/1993 | Wiese | | 5,942,214 A | 8/1999 | Lucas et al. |
| 5,232,691 A | 8/1993 | Lemole | | 5,948,390 A | 9/1999 | Nelson et al. |
| 5,240,696 A | 8/1993 | Van Der Ouderaa et al. | | 5,951,990 A | 9/1999 | Ptchelintsev |
| 5,244,651 A | 9/1993 | Kayane et al. | | 5,955,067 A | 9/1999 | Oge et al. |
| 5,258,183 A | 11/1993 | Grimberg | | 5,961,993 A | 10/1999 | Boussouira et al. |
| 5,310,546 A | 5/1994 | Douglas | | 5,965,137 A | 10/1999 | Petrus |
| 5,330,748 A | 7/1994 | Winston et al. | | 5,965,610 A | 10/1999 | Modak et al. |
| 5,330,749 A | 7/1994 | Giacin et al. | | 5,972,999 A | 10/1999 | Murad |
| 5,348,943 A | 9/1994 | Pickart | | 5,980,477 A * | 11/1999 | Kelly ............................. 602/77 |
| 5,352,438 A * | 10/1994 | N'Guyen et al. ............... 424/45 | | 5,994,403 A | 11/1999 | Donatiello |
| 5,382,431 A | 1/1995 | Pickart | | 6,019,976 A | 2/2000 | Bryant |
| 5,385,727 A | 1/1995 | Winston et al. | | 6,022,565 A | 2/2000 | Albert et al. |
| 5,401,730 A | 3/1995 | Sauvage et al. | | 6,030,605 A | 2/2000 | D'Ameila et al. |
| 5,424,077 A | 6/1995 | Lajoie | | 6,037,386 A | 3/2000 | Modak et al. |
| 5,439,863 A | 8/1995 | Bottcher et al. | | 6,046,178 A | 4/2000 | Silvetti, Sr. |
| 5,455,023 A | 10/1995 | Giacin et al. | | 6,060,079 A | 5/2000 | Freeman et al. |
| 5,466,470 A | 11/1995 | Lajoie | | 6,071,543 A | 6/2000 | Thornfeldt |
| 5,480,975 A | 1/1996 | Goldberg et al. | | 6,083,490 A | 7/2000 | Ellis et al. |
| 5,482,720 A | 1/1996 | Murphy et al. | | 6,086,666 A | 7/2000 | Noguchi et al. |
| 5,484,597 A * | 1/1996 | Slavtcheff et al. ............ 424/401 | | 6,103,247 A | 8/2000 | Boussouira et al. |
| 5,500,448 A | 3/1996 | Cummins et al. | | 6,103,273 A | 8/2000 | Antoun |
| 5,547,676 A | 8/1996 | Rocher et al. | | 6,113,636 A | 9/2000 | Ogle |
| 5,550,183 A | 8/1996 | Pickart | | 6,121,254 A | 9/2000 | Saint-Leger |
| 5,552,147 A | 9/1996 | Znaiden et al. | | 6,123,925 A | 9/2000 | Barry et al. |
| 5,554,375 A | 9/1996 | Pickart | | 6,132,743 A | 10/2000 | Kuroda et al. |
| 5,554,647 A | 9/1996 | Perricone | | 6,143,318 A | 11/2000 | Gilchrist et al. |
| 5,582,817 A | 12/1996 | Otsu et al. | | 6,149,947 A | 11/2000 | Hon et al. |
| 5,597,550 A | 1/1997 | Mo | | 6,183,785 B1 | 2/2001 | Westfall |
| 5,597,552 A | 1/1997 | Herms et al. | | 6,190,407 B1 | 2/2001 | Ogle et al. |
| 5,616,313 A | 4/1997 | Williams et al. | | 6,191,167 B1 | 2/2001 | Yu et al. |
| 5,622,724 A | 4/1997 | Bryce-Smith | | 6,200,580 B1 | 3/2001 | Horino et al. |
| 5,624,675 A | 4/1997 | Kelly | | 6,200,680 B1 | 3/2001 | Takeda et al. |
| 5,631,013 A | 5/1997 | Bergmann et al. | | 6,217,914 B1 | 4/2001 | Meisner |
| 5,632,972 A | 5/1997 | Williams et al. | | 6,221,403 B1 | 4/2001 | Nesbit |
| 5,645,840 A | 7/1997 | Lajoie et al. | | 6,224,896 B1 | 5/2001 | Redmond |
| 5,663,213 A | 9/1997 | Jones et al. | | 6,248,370 B1 | 6/2001 | Harris |
| 5,686,083 A | 11/1997 | Chamness | | 6,261,574 B1 | 7/2001 | Costello |
| 5,688,492 A | 11/1997 | Galley et al. | | 6,267,782 B1 | 7/2001 | Ogle et al. |
| 5,690,967 A | 11/1997 | Yu et al. | | 6,287,541 B1 | 9/2001 | Creeth et al. |
| 5,696,169 A | 12/1997 | Otsu et al. | | 6,303,651 B1 | 10/2001 | Hersh |
| 5,698,184 A | 12/1997 | Pickart | | 6,322,588 B1 | 11/2001 | Ogle et al. |
| 5,707,609 A | 1/1998 | Mo | | 6,322,820 B1 | 11/2001 | Simoneau |
| 5,708,023 A | 1/1998 | Modak et al. | | 6,331,567 B1 | 12/2001 | Watson et al. |
| 5,728,404 A | 3/1998 | Von Rheinbaben et al. | | 6,361,800 B1 | 3/2002 | Cooper et al. |
| 5,747,005 A | 5/1998 | Barels et al. | | 6,375,942 B1 | 4/2002 | Rico |
| 5,753,637 A | 5/1998 | Fried | | 6,395,301 B1 | 5/2002 | Cantin |
| 5,762,945 A | 6/1998 | Ashley et al. | | 6,416,744 B1 | 7/2002 | Robinson et al. |
| 5,780,020 A | 7/1998 | Peterson et al. | | 6,444,699 B2 | 9/2002 | Meisner |
| 5,795,574 A | 8/1998 | Breton et al. | | 6,451,294 B1 | 9/2002 | Simon |
| 5,798,121 A | 8/1998 | Cauwet et al. | | 6,471,972 B1 | 10/2002 | Bonte et al. |

| | | |
|---|---|---|
| 6,475,526 B1 | 11/2002 | Smith |
| 6,517,849 B1 | 2/2003 | Seger et al. |
| 6,521,265 B1 | 2/2003 | Patterson |
| 6,558,710 B1 | 5/2003 | Godfrey |
| 6,579,541 B2 | 6/2003 | Antelman |
| 6,582,684 B1 | 6/2003 | Abrahamson |
| 6,582,710 B2 | 6/2003 | Deckers et al. |
| 6,592,852 B1 | 7/2003 | Ryles et al. |
| 6,599,513 B2 | 7/2003 | Deckers et al. |
| 6,607,716 B1 | 8/2003 | Smith et al. |
| 6,627,178 B1 | 9/2003 | Cawthon |
| 6,660,306 B2 | 12/2003 | Peshoff |
| 6,663,852 B2 | 12/2003 | Simon |
| 6,680,073 B1 | 1/2004 | Tarbet |
| 6,682,720 B2 | 1/2004 | Ryles et al. |
| 6,696,071 B2 | 2/2004 | Kelly |
| 6,726,919 B2 | 4/2004 | Pace et al. |
| 6,730,309 B2 | 5/2004 | Horino |
| 6,730,329 B1 | 5/2004 | Smith |
| 6,743,416 B2 | 6/2004 | Riedl |
| 6,750,209 B1 | 6/2004 | Hudson et al. |
| 6,773,698 B1 | 8/2004 | Melinte et al. |
| 6,780,439 B2 | 8/2004 | Wilk |
| 6,800,301 B2 | 10/2004 | Smith |
| 6,833,362 B2 | 12/2004 | Bowen, Jr. et al. |
| 6,844,012 B1 | 1/2005 | Forceville et al. |
| 6,849,277 B2 | 2/2005 | Roig |
| 6,855,341 B2 | 2/2005 | Smith |
| 6,858,201 B2 | 2/2005 | Pickart |
| 6,929,800 B2 | 8/2005 | Salman |
| 6,932,976 B2 | 8/2005 | Brooks |
| 6,939,568 B2 | 9/2005 | Burrell et al. |
| 6,942,878 B2 | 9/2005 | Ishii et al. |
| 6,949,248 B2 | 9/2005 | Nishihama |
| 6,949,249 B2 | 9/2005 | Healy et al. |
| 6,964,782 B1 | 11/2005 | Smith et al. |
| 6,989,156 B2 | 1/2006 | Gillis |
| 7,008,647 B2 | 3/2006 | Burrell et al. |
| 7,014,870 B1 | 3/2006 | Hon et al. |
| 7,026,308 B1* | 4/2006 | Gavin et al. ............ 514/188 |
| 7,049,339 B2 | 5/2006 | Thomson |
| 2001/0014356 A1 | 8/2001 | Yoshida et al. |
| 2001/0041193 A1 | 11/2001 | Meisner |
| 2002/0001629 A1 | 1/2002 | Voellmy |
| 2002/0031557 A1 | 3/2002 | Meisner |
| 2002/0114847 A1 | 8/2002 | Peshoff |
| 2002/0182244 A1 | 12/2002 | Jackson |
| 2003/0004564 A1 | 1/2003 | Elkins et al. |
| 2003/0026848 A1 | 2/2003 | Joshi |
| 2003/0035825 A1 | 2/2003 | Shiau et al. |
| 2003/0059484 A1 | 3/2003 | Bonte et al. |
| 2003/0068351 A1 | 4/2003 | Roig |
| 2003/0069369 A1 | 4/2003 | Belenkaya et al. |
| 2003/0072819 A1 | 4/2003 | Tao |
| 2003/0077304 A1 | 4/2003 | McCadden |
| 2003/0077332 A1 | 4/2003 | Godfrey |
| 2003/0082219 A1 | 5/2003 | Warren et al. |
| 2003/0082223 A1 | 5/2003 | Healy et al. |
| 2003/0099721 A1 | 5/2003 | Yoshida et al. |
| 2003/0118623 A1 | 6/2003 | De Paoli Ambrosi |
| 2003/0133991 A1 | 7/2003 | Monroe et al. |
| 2003/0138497 A1 | 7/2003 | Sakuma et al. |
| 2003/0161892 A1 | 8/2003 | McFarland |
| 2003/0166510 A1* | 9/2003 | Pickart ............ 514/6 |
| 2003/0190371 A1 | 10/2003 | Graaf et al. |
| 2003/0194446 A1 | 10/2003 | Akes et al. |
| 2003/0199488 A1 | 10/2003 | Trotta |
| 2003/0215412 A1 | 11/2003 | Waugh et al. |
| 2003/0215522 A1 | 11/2003 | Johnson et al. |
| 2003/0224023 A1 | 12/2003 | Faryniarz et al. |
| 2003/0224027 A1 | 12/2003 | Faryniarz et al. |
| 2004/0022863 A1 | 2/2004 | Hamtini |
| 2004/0028708 A1 | 2/2004 | Brooks |
| 2004/0033270 A1 | 2/2004 | Kropf et al. |
| 2004/0037910 A1 | 2/2004 | Hon et al. |
| 2004/0058011 A1 | 3/2004 | Petersson |
| 2004/0058015 A1 | 3/2004 | Tao |
| 2004/0062730 A1 | 4/2004 | Kurosawa et al. |
| 2004/0062817 A1 | 4/2004 | Peshoff |
| 2004/0076686 A1 | 4/2004 | Riesinger |
| 2004/0091551 A1 | 5/2004 | Damji |
| 2004/0101541 A1 | 5/2004 | Heffernan et al. |
| 2004/0109902 A1 | 6/2004 | McDonagh et al. |
| 2004/0131700 A1 | 7/2004 | Cifra et al. |
| 2004/0156875 A1 | 8/2004 | Fabre et al. |
| 2004/0157921 A1 | 8/2004 | Cifra et al. |
| 2004/0170701 A1 | 9/2004 | Carter |
| 2004/0170703 A1 | 9/2004 | Hoekstra et al. |
| 2004/0170712 A1 | 9/2004 | Sadek El Mogy |
| 2004/0175433 A1 | 9/2004 | Thomson |
| 2004/0185015 A1 | 9/2004 | Zhang et al. |
| 2004/0185074 A1 | 9/2004 | Faryniarz et al. |
| 2004/0202689 A1 | 10/2004 | Subramanyan et al. |
| 2004/0220100 A1 | 11/2004 | Waugh et al. |
| 2004/0253321 A1 | 12/2004 | Fechner et al. |
| 2004/0258769 A1 | 12/2004 | Barker et al. |
| 2005/0048010 A1 | 3/2005 | Klis et al. |
| 2005/0069506 A1 | 3/2005 | Katusic et al. |
| 2005/0069588 A1 | 3/2005 | Taal |
| 2005/0074425 A1 | 4/2005 | Waugh et al. |
| 2005/0079229 A1 | 4/2005 | Cawthon |
| 2005/0100571 A1 | 5/2005 | Keyes |
| 2005/0123620 A1 | 6/2005 | Chiou |
| 2005/0136129 A1 | 6/2005 | Verheul-Koot et al. |
| 2005/0175719 A1 | 8/2005 | Sun et al. |
| 2005/0202054 A1 | 9/2005 | Faryniarz et al. |
| 2005/0234239 A1 | 10/2005 | Taillefer et al. |
| 2005/0238730 A1 | 10/2005 | Le Fur et al. |
| 2006/0029682 A1 | 2/2006 | Monroe et al. |
| 2006/0036007 A1 | 2/2006 | Hsieh et al. |
| 2006/0089407 A1 | 4/2006 | Maurer |
| 2007/0032751 A1 | 2/2007 | Roman |

FOREIGN PATENT DOCUMENTS

| | | | |
|---|---|---|---|
| WO | WO 94/14408 | * | 7/1994 |
| WO | WO 02/100383 | | 12/2002 |
| WO | WO 2004/039238 A2 | | 5/2004 |
| WO | WO 2004/039238 A3 | | 5/2004 |

OTHER PUBLICATIONS

Hernández-Molina M., "A phase transition in the novel three-dimensional compound [Eu$_2$(mal)$_2$(H$_2$O)$_6$] (H$_2$mal=malonic acid)", *J.Chem.Soc., Dalton Trans.* 2002, vol. 18, 3462.

Rodríguez-Martín, Y., "Structural Versatility of the Malonate Ligand as a Tool for Crystal Engineering in the Design of Molecular Magnets", *Cryst. Eng. Comm.* 2002, vol. 4, No. 87, 522-535.

Sanchiz, J., "Ferromagnetic coupling in the malonato-bridged copper(II) chains {[Cu(Im)$_2$(mal)]}$_n$ and {[Cu(2-MeIm)$_2$(mal)]}$_n$ (H$_2$mal=Malonic Acid, Im=imidazole and 2-MeIm=2-methylimidazole)", *New J. Chem.* 2002, vol. 26, 1624.

Rodríguez-Martín, Y., "The flexibility of molecular components as a suitable tool in designing extended magnetic systems", *Cryst. Eng. Comm.* 2002, vol. 4, No. 73, 440-446.

Ruiz-Pérez, C., "Dimensionally controlled hydrogen-bonded nanostructures: Synthesis, structure, thermal and magnetic behaviour of the tris-(chelated)nickel(II) complex [Ni(bipy)$_3$]Cl$_2$.5.5H$_2$O (bipy=2,2'-bipyridine)", *Inorg. Chim. Acta.* 2002, vol. 336, 131-136.

Rodríguez-Martín, Y., "Extended network via hydrogen bond linkages of coordination compounds: Synthesis, crystal structure and thermal behavior of the complexes [MII(L)$_2$(NO$_3$)$_2$] (MII=Cu, Co) and [Ni(L)$_2$(H$_2$O)]•(NO$_3$)$_2$ (L=malonamide)", *Inorganica Chimica Acta.* vol. 328, 169-178 (2002).

Rodríguez-Martín, Y., "Synthesis, crystal structure and magnetic properties of [Cu(bpym)(mal)(H$_2$O)]•6H$_2$O and [Cu$_2$(bpym)(mal)$_2$(H$_2$O)$_2$]•4H$_2$O (bpym=2,2'-bipyrimidine, H2mal=Malonic Acid)", *Inorganica Chimica Acta.* vol. 326, 20-26 (2001).

Delgado, F., "Alkali-Templated Malonate Copper (II) Complexes", *Acta Cryst.* A61, C358 (2005).

Naumov, P, et al., "The Crystal Structure of Copper (II) Malonate Trihydrate", *CCACAA*, vol. 75, No. 3, 701-711 (2002).

Filippova I.G., "Polymorphism of Coordination Compounds with Malonic Añid", *Moldavian Journal of the Physical Sciences*, 1vol. 1, No. 3, 87-93 (2002).

Tinker, D. et al., "Role of Selected Nutrients in Synthesis, Accumulation, and Chemical Modification of Connective Tissue Proteins", *Physiolgical Reviews*, vol. 65, No. 3, 607-657 (1985).

Philip, B., et al., "Dietary Zinc & Levels of Collagen, Elastin & Carbohydrate Components of Glycoproteins of Aorta, Skin & Cartilage in Rats", *Indian J. Exp. Biol.*, vol. 16, 370-372 (1978).

Homsy, R. et al., "Characterization of Human Skin Fibroblasts Elastase Activity", *J. Invest. Dermatol*, vol. 91, 472-477 (1988).

* cited by examiner

US 7,927,614 B2

ANTI-AGING TREATMENT USING COPPER AND ZINC COMPOSITIONS

CROSS REFERENCE TO RELATED APPLICATION

This Application claims priority benefit of U.S. Provisional Application No. 60/764,967 filed Feb. 3, 2006 the entire disclosure of which is incorporated herein by this reference.

BACKGROUND

1. Technical Field

This disclosure relates to the use of compositions containing copper, zinc and/or copper-zinc active ingredients for pharmaceutical and cosmeceutical purposes.

2. Background of the Invention

Aging is a phenomenon which occurs in all living things. Unfortunately, with age comes a multitude of undesirable skin conditions which can adversely affect the appearance and health of skin. For example, as skin ages it becomes more susceptible to symptoms such as, inter alia, dryness, itchiness, thinning or thickening, wrinkles and/or fine lines, hyperpigmentation, telangietasias, and the like. Although there are known treatments for alleviating and curing age related skin conditions, known skin treatments are problematic in that results vary from patient to patient. Moreover, no one treatment, if ever, obtains maximum benefit for every patient. As a result, novel skin treatments are continuously sought after to thwart undesirable age related skin conditions.

Accordingly, there remains room for improvement in skin treatment regimens that enhance aged skin. What are needed are new skin care compositions and methods for treating age related skin conditions.

SUMMARY

Active ingredients such as copper-zinc salts of multifunctional organic acids and formulations containing them may be used to treat age related skin conditions. The copper constituent and zinc constituent, which may be cations, may be combined within a single molecule or used individually in separate molecules during topical application to treat age related skin conditions. For example, copper and zinc constituents may be topically applied simultaneously to the skin of the user in order to combine the catalytic properties of each constituent. Moreover, the copper and zinc constituents may be topically applied in the same molecule to combine the catalytic properties of each constituent. Accordingly, the combined application of copper and zinc constituents in the same topical treatment provides enhanced biological activity than the use of either constituent alone.

Skin having one or more undesirable age related conditions is treated in accordance with the present disclosure by the topical application of one or more active ingredients thereto. For example, compositions containing copper-zinc malonates can be directly applied to skin in need of treatment. Such conditioning by application of copper-zinc active ingredients may reduce or eliminate undesirable age related skin conditions, and promote or stimulate collagen, elastin, tropoelastin, and/or elastic fiber production in the dermis to make aged skin healthier, and/or appear younger.

In addition, dermatological treatment regimens in accordance with the present disclosure may improve characteristics of a user's aged skin. The regimens include the repeated topical application of one or more copper-zinc active ingredients. Suitable corrective compositions include, for example, compositions which help to reduce or eliminate age related conditions. In embodiments, compositions including a single molecule having both copper and zinc constituents are applied to the skin to increase levels of collagen, elastin, tropoelastin, and/or elastic fibers in the dermis layer. The resulting increase can improve the appearance of skin and/or give a more youthful look.

These and other aspects of this disclosure will be evident upon reference to the following detailed description.

DETAILED DESCRIPTION OF PREFERRED EMBODIMENTS

Figure 1:
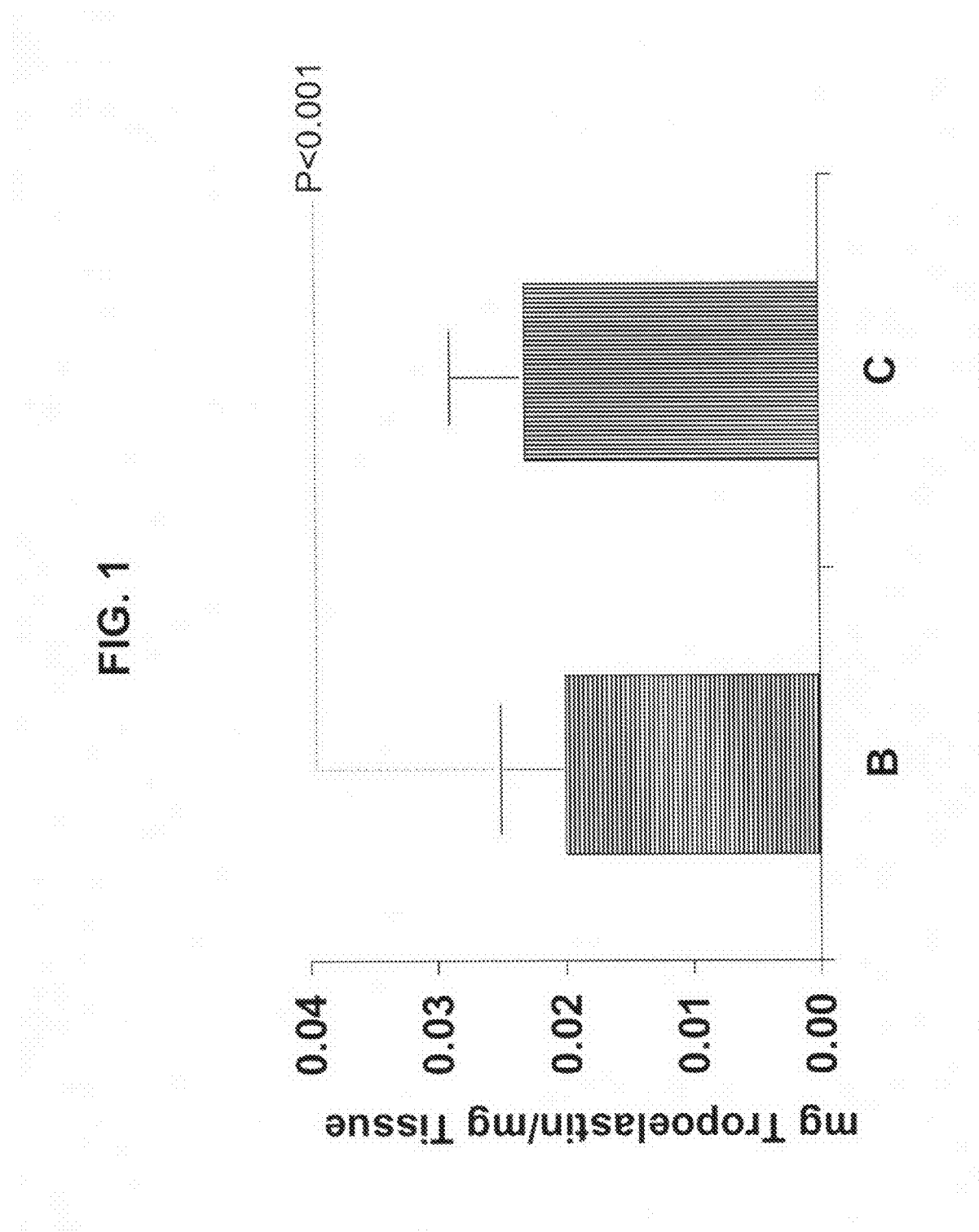
FIG. 1 is a histogram comparing tropoelastin levels in skin after application of a 0.1% copper-zinc malonate formulation to skin at baseline (B) and at four weeks (C).

Active ingredients are used in accordance with the present disclosure to treat age related skin conditions. As copper and zinc are biologically needed by the body to catalyze the production of collagen and elastin in the dermis, active ingredients having copper, zinc and/or copper-zinc constituents can be topically applied to treat age related skin conditions. For example, bimetal complexes having copper and/or zinc constituents can be applied to skin to penetrate the dermis to stimulate production of collagen, elastin, tropoelastin and/or elastic fibers resulting in improved skin appearance.

Suitable active ingredients for use in accordance with the present disclosure include non-toxic compounds containing both copper and zinc. Such copper, zinc, and copper-zinc active ingredients include, but are not limited to, water soluble compounds that contain both copper and zinc. The water-soluble copper-zinc compounds include any copper-zinc salts formed from reacting any multifunctional organic or inorganic acid with any zinc or copper metal and/or their metallic bases. The organic acid can be aromatic or aliphatic. Suitable non-limiting examples of the water-soluble copper-zinc compounds include copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, and combinations thereof. Suitable non-water soluble copper-zinc compounds include any copper-zinc salts found from reacting any multifunctional water insoluble organic acid with zinc or copper metal and/or their metallic bases. Accordingly, suitable non-limiting examples of the non-water soluble copper-zinc compounds include copper-zinc adipate, copper-zinc pimelate, copper-zinc suberate, copper-zinc azelate, copper-zinc sebacate, copper-zinc dodecanoate, and combinations thereof. In embodiments, copper-zinc salts of organic multicarboxylic acids are suitable for use in accordance with the present disclosure. Accordingly, it is envisioned that multifunctional organic acids such as carboxylic acids may be reacted with any zinc or copper metal and/or their metallic bases to form the active ingredient of the present disclosure. In embodiments, the molar ratio of copper to zinc in the copper-zinc active ingredient is from about 1:1 to about 3:1. In other embodiments, the molar ratio of copper to zinc in the copper-zinc active ingredient is from about 1:1 to about 2:1.

In particular embodiments, non-limiting examples of suitable active ingredients include one or more copper-zinc malonates. As used herein "copper-zinc malonate" refers to any salt substances formed from malonic acid having copper and zinc constituents at various mole ratios of copper and zinc in the same molecule. For example, in embodiments, the molar ratio of copper to zinc in the copper-zinc malonate active ingredient is from about 1:1 to about 3:1. In other embodiments, the molar ratio of copper to zinc in the copper-zinc malonate active ingredient is from about 1:1 to about 2:1. In embodiments, copper-zinc malonate includes about 16.5% copper and about 12.4% zinc. In general, the copper-zinc malonate active ingredients used in accordance with the present disclosure include ingredients that are compounds of copper and zinc with malonic acid. Non-limiting examples of suitable ingredients for the formation of suitable copper-zinc malonates include, but are not limited to, malonic acid, zinc base, copper base, and water.

In forming suitable copper-zinc malonates for use in accordance with the present disclosure, malonic acid is present in amounts that will react with metal cations such as copper and zinc in an aqueous solution. Suitable amounts of malonic acid also include excess amounts in relation to the amount of copper and zinc cations to force reactions. In embodiments, malonic acid is present in a 3:1:1 molar ratio in relation to the copper and zinc constituents. Two or more salts containing copper and zinc constituents can be present in amounts that will react with malonic acid in an aqueous solution. Suitable salts that may be employed in making copper-zinc malonate active ingredients in accordance with this disclosure include metal salts containing complex-forming metal ions of copper and/or zinc. Non-limiting examples of suitable metal basic salts are: copper (I) and (II) salts such as copper carbonate, copper oxide, and copper hydroxide; and zinc salts such as zinc carbonate, zinc oxide, zinc hydroxide, metallic copper and metallic zinc. In embodiments, the reaction media includes two metallic salts, such as cupric carbonate ($CuCO_3 \cdot Cu(OH)_2$), zinc carbonate ($3Zn(OH)_2 \cdot 2ZnCO_3$), or metallic zinc and metallic copper.

In embodiments, any copper salt, zinc salt and/or combinations of copper salt and zinc salt may be topically applied as an active ingredient in amounts sufficient to reduce or eliminate undesirable age related skin conditions, stimulate collagen, elastin tropoelastin and/or elastic fiber production in the dermis and/or make aged skin healthier and appear younger. Additional suitable non-limiting examples of copper and/or zinc salts which may be used to treat skin include copper (II) malonate and any hydrated form thereof such as copper (II) malonate dihydrate, copper (II) malonate trihydrate, and copper malonate tetrahydrate. Other suitable non-limiting examples of suitable copper and/or zinc salt active ingredients for treating age related skin conditions in accordance with the present disclosure include copper or zinc salts of citrate, oxalate, tartarate, malate, succinate, malonate, maleate, aspartate, glutamate, glutarate, fumarate, glucarate, polyacrylic acid, adipate, pimelate, suberate, azelate, sebacate, dodecanoate. Combinations thereof are also possible.

The active ingredient or ingredients may be combined with numerous ingredients to form products to be applied to the skin, or other tissues of humans or other mammals. Such products may include a dermatologically or pharmaceutically acceptable carrier or diluent, vehicle or medium, for example, a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. In embodiments, compositions in accordance with the present disclosure can contain any ingredient conventionally used in cosmetics and/or dermatology.

As an illustrative example, compositions can be formulated to contain active ingredient in amounts from about 0.001 to about 5% by weight of the total composition. In embodiments, products can be formulated to contain active ingredient in an amount from about 0.05 to about 1% by weight of the total composition. In other embodiments, the amount of active ingredient is from about 0.1 to about 0.5% by weight of the total composition. In such embodiments, the copper or zinc salt and/or copper-zinc present may be in a pharmaceutically acceptable salt form.

In embodiments, products containing active ingredients in accordance with the present disclosure can be in the form of solutions, emulsions (including microemulsions), suspensions, creams, fluid cream, oils, lotions, gels, powders, or other typical solid or liquid compositions used for treatment of age related skin conditions. Such compositions may contain, in addition to the copper and/or zinc salts and/or copper-zinc salts in accordance with this disclosure, other ingredients typically used in such products, such as other active cosmetic substances such as retinol, retinol derivatives, allantoin, tocopherol, tocopherol derivatives, niacinamide, phytosterols, isoflavones, panthenol, panthenol derivatives, bisabolol, farnesol, and combinations thereof, other active drug substances such as corticosteroid, metronidazole, sulfacetamide, sulfur, and combinations thereof, antioxidants, antimicrobials, coloring agents, detergents, dyestuffs, emulsifiers, emollients, fillers, fragrances, gelling agents, hydration agents, moisturizers, odor absorbers, natural or synthetic oils, penetration agents, powders, preservatives, solvents, surfactants, thickeners, viscosity-controlling agents, water, distilled water, waxes, and optionally including anesthetics, anti-itch actives, botanical extracts, conditioning agents, darkening or lightening agents, glitter, humectant, mica, minerals, polyphenols, phytomedicinals, silicones or derivatives thereof, skin protectants, sunblocks, vitamins, and mixtures or combinations thereof. Such compositions may also contain, in addition to the copper or zinc salts and/or copper-zinc salts in accordance with this disclosure, one or more: fatty alcohols, fatty acids, organic bases, inorganic bases, wax esters, steroid alcohols, triglyceride esters, phospholipids, polyhydric alcohol esters, fatty alcohol ethers, hydrophilic lanolin derivatives, hydrophilic beeswax derivatives, cocoa butter waxes, silicon oils, pH balancers, cellulose derivatives, hydrocarbon oils, or mixtures and combinations thereof.

In embodiments, product forms can be formulated to contain humectant in amounts from about 1% to about 15% by weight of the total composition. For example glycerine can be added to the composition in amounts from about 1% to about 15% by weight of the total composition. In particular embodiments, glycerine can be added to the composition in amounts from about 1% to about 5% by weight of the total composition.

In embodiments, product forms can be formulated to contain solvent in amounts from about 1% to about 45% by weight of the total composition. For example petroleum derivatives such as propylene glycol can be added to the composition in amounts from about 1% to about 45% by weight of the total composition. In particular embodiments, propylene glycol can be added to the composition in amounts from about 15% to about 30% by weight of the total composition.

In embodiments, product forms can be formulated to contain water in amounts from about 40% to about 99% by weight of the total composition. For example distilled water can be added to the composition in amounts from about 40% to about 99% by weight of the total composition. In particular embodiments, distilled water can be added to the composition in amounts from about 65% to about 80% by weight of the total composition.

The present active ingredients and formulations containing them in accordance with the present disclosure can be topically applied to skin in need of improvement in amounts sufficient to reduce or eliminate undesirable age related skin conditions, such as via stimulation of collagen, elastin, tropoelastin and/or elastic fiber production. As used herein the word "treat," "treating" or "treatment" refers to using the compositions of the present disclosure prophylactically to prevent outbreaks of any undesirable age related skin conditions, or therapeutically to ameliorate an existing undesirable age related skin condition. A number of different treatments are now possible, which reduce and/or eliminate age related skin conditions such as wrinkles.

As used herein "age related skin condition" refers to any detectable skin manifestations caused by skin aging. Such manifestations can appear due to a number of factors such as, for example, chronological aging, environmental damage, and/or other diseased or dysfunctional state. Non-limiting examples of such manifestations include the development of dryness, itchiness, thinning, thickening, wrinkling, including both fine superficial wrinkles and coarse deep wrinkles, skin lines, crevices, bumps, large pores, scaliness, flakiness and/or other forms of skin unevenness or roughness, hyperpigmentation, mottled appearance, decreased healing times, cherry angioma, telangietasias, senile development, actinic purpura development, seborrheic keratoses, actinic keratoses, fatty tissue formation, fatty tissue deterioration, increased collagen, elastin, tropoelastin, and elastic fiber content, decreased collagen, elastin, tropoelastin or elastic fiber content, and combinations thereof. Such manifestations further include undesirable tactile conditions such as loss of skin elasticity, sagging, loss of skin firmness, loss of skin tightness, loss of skin recoil from deformation, and/or sallowness. Such manifestations further include undesirable visible conditions such as hyperpigmented skin regions such as age spots and freckles, keratoses, abnormal differentiation, hyperkeratinization, stretch marks, discoloration, blotching, and combinations thereof. It is understood, that the listed age related skin conditions are non-limiting and that only a portion of the skin conditions suitable for treatment in accordance with the present disclosure are listed herein.

In embodiments, compositions for use in accordance with the present disclosure contain one or more active ingredients capable of contacting skin with copper and/or zinc in an effective amount to improve undesirable age related skin conditions. As used herein "effective amount" refers to an amount of a compound or composition having active ingredients such as those having copper, zinc and/or copper-zinc constituents in accordance with the present disclosure that is sufficient to induce a particular positive benefit to skin having an age related skin condition. The positive benefit can be health-related, or it may be more cosmetic in nature, or it may be a combination of the two. In embodiments, the positive benefit is achieved by contacting skin with a combination of copper and zinc which can be in the form of copper and zinc ions, and/or one or more salts having copper and zinc constituents, to improve an age related skin condition. In embodiments, the positive benefit is achieved by contacting skin with one or more active ingredients to enhance tropoelastin levels and/or increase insoluble elastic fibers in skin. In embodiments, the positive benefit is achieved by contacting skin with one or more active ingredients to increase insoluble elastin levels and/or reestablish firmness of skin. In embodiments, the positive benefit is achieved by contacting skin with one or more active ingredients to improve wrinkles.

The particular active ingredient or ingredients employed, and the concentration in the compositions, generally depends on the purpose for which the composition is to be applied. For example, the dosage and frequency of application can vary depending upon the type and severity of the age related skin condition.

Treatments in accordance with the present disclosure contact skin with one or more active ingredients such as those containing copper and zinc in an effective amount to improve undesirable age related skin conditions. In embodiments, patients are treated by topically applying to skin suffering from an age related condition, one or more copper-zinc malonates. In embodiments, patients are treated by topically applying to skin suffering from an age related condition, one or more copper, zinc and/or copper-zinc salts. The active ingredient is applied until the treatment goals are obtained. However, the duration of the treatment can vary depending on the severity of the condition. For example, treatments can last several weeks to months depending on whether the goal of treatment is to reduce or eliminate an age related skin condition.

Treatments in accordance with the present disclosure contact skin with one or more active ingredients such as those containing copper and zinc in an effective amount to increase collagen, elastin (insoluble/soluble), elastic fiber and/or tropoelastin levels therein. As used herein "elastin" refers to a protein in the skin that helps maintain resilience and elasticity. Generally, elastin is a protein in connective tissue that is elastic and allows tissues in the body, including skin, to resume their shape after stretching or contracting. For example, when pressure is applied to skin to change its shape, elastin helps skin to return to its original shape. Elastin may be made by linking multiple tropoelastin protein molecules to make a large insoluble cross-linked aggregate. As used herein "tropoelastin" refers to a water-soluble precursor to the elastin molecule, having a molecular weight of about 70000 Daltons. As used herein, "collagen" refers to a fibrous protein that contributes to the physiological functions of connected tissues in the skin, tendon, bones, and cartilage. Generally, the structural unit is tropocollagen composed of 3-polypeptide chains, designated A1, A2, and A3 that form a triple helical structure stabilized by hydrogen bonds. The term collagen further refers to collagen types, such as type I collagen, type II collagen, and type III collagen.

In embodiments, patients are treated by topically applying to skin in need of collagen, elastin, tropoelastin and/or elastic fibers one or more copper, zinc and/or copper-zinc salts, such as copper-zinc malonate. The active ingredient is applied until the treatment goals are obtained. However, the duration of the treatment can vary depending on the severity of the condition. For example, treatments can last several weeks to months depending on whether the goal of treatment is to promote or repair collagen, elastin, tropoelastin and/or elastic fiber levels in the skin. In treatment embodiments, 1 to 5 drops of a composition containing 0.1% copper-zinc malonate may be applied to wrinkled skin twice a day for 4 weeks. In such treatments, some users should expect tropoelastin levels in the skin to increase in amounts of about 5% to about 30% and/or insoluble elastin content to be increased in amounts of about 20% to about 30%. Accordingly, some users should expect the treatment to diminish wrinkles and cause the skin to appear healthier and look younger. Moreover, some users should expect firmness of the wrinkled skin to be reestablished.

In embodiments, the active agents are applied for cosmetic purposes only.

In some embodiments, use of a compound including copper-zinc ingredients such as copper-zinc malonate may be included in the manufacture of a medicament for treatment of an age related skin condition. In such embodiments, copper-zinc ingredients described in accordance with the present disclosure can be manufactured into a pure medicament, compositions containing medicament, and/or formulations containing medicament and any excipients and/or ingredients described herein.

The following non-limiting examples further illustrate methods in accordance with this disclosure.

Example 1

A 72 year old woman is suffering from wrinkling on her face. A gel composition suitable for treatment of skin containing an effective amount of copper-zinc malonate active ingredient is routinely applied to her face twice daily. Wrinkling is reduced or eliminated.

Example 2

A copper-zinc malonate formulation has the following make-up:

| COMPONENT | % BY WEIGHT |
|---|---|
| Copper-zinc malonate* (Active ingredient) | 0.1% |
| Glycerine | 3.0% |
| Propylene Glycol | 25.0% |
| Distilled Water | 71.9% |

*Copper-zinc malonate was made by mixing 1 mole Zn/1 mole Cu/3 moles malonic acid.

Example 3

A 28-day, split-face, right and left forearm punch biopsy study to investigate the efficacy of composition of Example 2 to increase the collagen, elastin, tropoelastin and/or elastic fiber levels in the skin was performed. Pre-determined treatment areas were assigned around eyes and on forearms.

The following application protocol was used on some subjects:
Treatment Protocol:
A trained technician applied the composition of Example 2 to pre-assigned eye areas and forearm areas wearing a clear polyethylene disposable glove to rub product uniformly onto the test site. Product and total amounts applied were:

| | |
|---|---|
| Formulation of Example 2 applied to eye area | 1 drop |
| Formulation of Example 2 applied to forearm | 2 drops |
| Formulation of Example 2 without active applied to eye area | 1 drop |
| Formulation of Example 2 without active applied to forearm | 2 drops |

After application, the subjects were instructed to avoid washing areas for a minimum of 8 hours.

Treatments for all subjects included daily product applications (Monday-Friday) at the clinic starting at baseline (Day 1) through Day 27. Skin elasticity measurements were taken by a trained technician using the Cutometer® (Courage+Khazaka) as well as ultrasound recordings. Cutometer and ultrasound measurements were taken at baseline (Day 1), week 2 (Day 14), and week 4 (Day 28). Punch biopsy skin samples were obtained at baseline and at week 4 (Day 28) on the right and left forearms of some subjects. A total of 2 punch biopsies (1 on the right forearm and 1 on the left forearm) were taken by a Board Certified Dermatologist at each visit.

Results:

Individuals that utilized the formulation of example 2 (with active ingredient) show increased levels tropoelastin and elastic fibers in skin after 27 days of product application. For example, elevated levels of tropoelastin were observed. Referring to FIG. 1, a histogram compares tropoelastin levels at baseline (B) and at four weeks (C). The results demonstrate that the application of copper-zinc malonate composition of Example 2, increases tropoelastin levels by approximately 19%. Moreover, for 8 of 13 subjects where composition of Example 2 with active ingredient was applied to the forearm, an increase in insoluble elastic fibers of approximately 29% was observed.

Figures 2A, 2B:
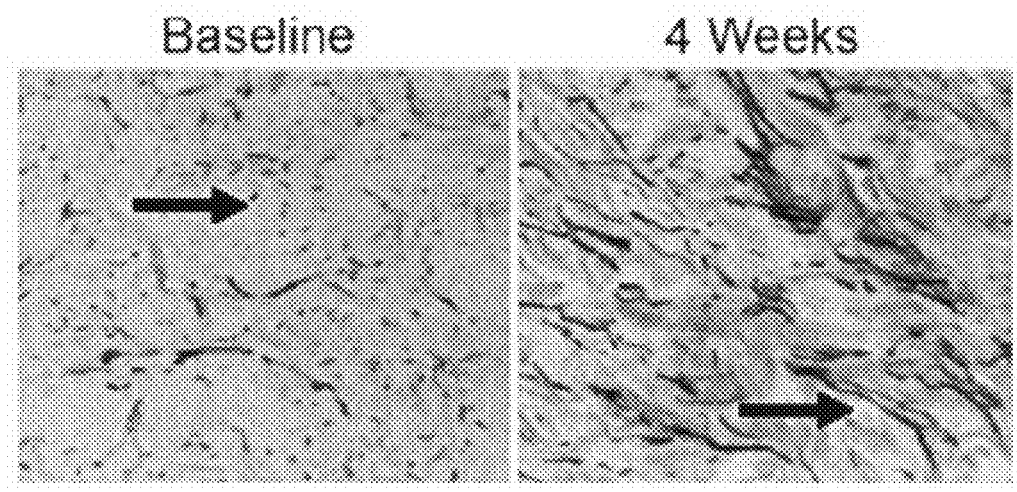
FIGS. 2A and 2B are photographs comparing elastic fibers in skin after application of a 0.1% copper-zinc malonate formulation to skin at baseline (FIG. 2A) and at four weeks (FIG. 2B).

Referring now to FIGS. 2A and 2B, photographs of skin tissue comparing elastic fibers at baseline (arrow in FIG. 2A) to elastic fibers after four weeks (arrow in FIG. 2B) are shown. Accordingly, treatment with composition in accordance with Example 2 increased elastic fibers in skin.

Figures 3A, 3B, 3C:
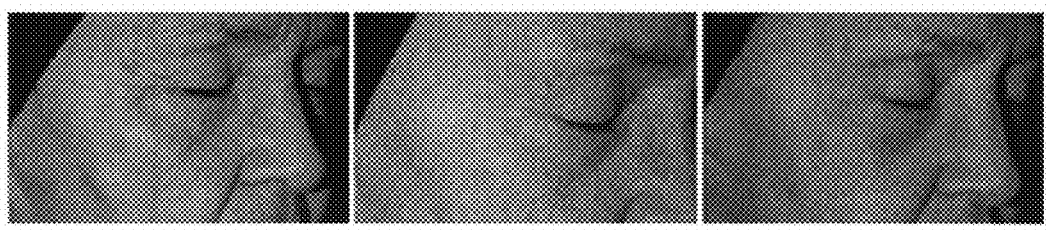
FIGS. 3A, 3B and 3C are photographs that illustrate a comparison of wrinkles over treatment course which topically applied a composition in accordance with the present disclosure (0.1% copper-zinc malonate) to skin.

Referring now to FIGS. 3A, 3B, and 3C, a series of progressive photographs are shown of the face of a 67 year old female having Fitzpatrick Type I skin type at baseline, two weeks, and 4 weeks respectively during treatment in accordance with the present disclosure. Here, the treatment included applying 1 drop of a formulation in accordance with Example 2 to skin immediately adjacent to the right eye (O.D.). The photographs show reduced wrinkling of skin around the right eye where composition in accordance with the present disclosure (Example 2) was applied. Skin in FIG. 3C after four weeks of treatment looked healthier and younger and reduced wrinkling was observed.

Figures 4A, 4B, 4C:
FIGS. 4A, 4B and 4C are photographs that illustrate a comparison of wrinkles over treatment course which topically applied a composition in accordance with the present disclosure (0.1% copper-zinc malonate) to skin.

Referring now to FIGS. 4A, 4B, and 4C a series of progressive photographs are shown of the face of a 50 year old female having Fitzpatrick Type I skin type at baseline, two weeks, and 4 weeks respectively during treatment in accordance with the present disclosure. Here, the treatment included applying 1 drop of a formulation in accordance with Example 2 to skin immediately adjacent to the left eye (O.S.). The photographs show reduced wrinkling of skin around the left eye where composition in accordance with the present disclosure (Example 2) was applied. Skin in FIG. 4C after four weeks of treatment looked healthier and younger and reduced wrinkling was observed.

Figures 5A, 5B, 5C:
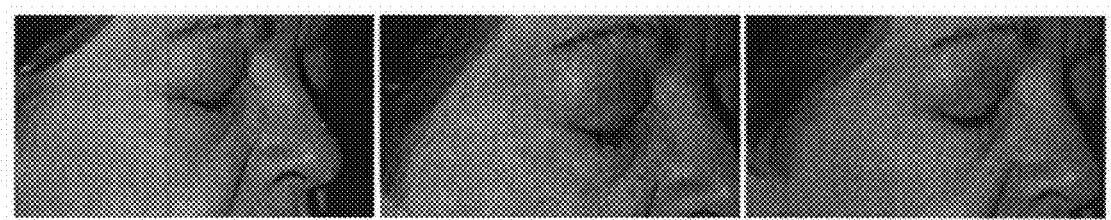
FIGS. 5A, 5B and 5C are photographs that illustrate a comparison of wrinkles over treatment course which topically applied a composition in accordance with the present disclosure (0.1% copper-zinc malonate) to skin.

Referring now to FIGS. 5A, 5B, and 5C a series of progressive photographs are shown of the face of a 59 year old female having Fitzpatrick Type I skin type at baseline, two weeks, and 4 weeks respectively during treatment in accordance with the present disclosure. Here, the treatment included applying 1 drop of a formulation in accordance with Example 2 to skin immediately adjacent to the right eye (O.D.). The photographs show reduced wrinkling of skin around the right eye where composition in accordance with the present disclosure (Example 2) was applied. Skin in FIG. 5C after four weeks of treatment with composition of Example 2 looked healthier and younger and reduced wrinkling was observed.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method comprising topically applying to a user's skin a composition comprising a copper-zinc carboxylic acid salt having copper and zinc cations in the same molecule.

2. A method as in claim 1 wherein the copper-zinc carboxylic acid salt having copper and zinc cations in the same molecule comprises copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azelate, copper-zinc sebacate, copper-zinc dodecanoate, or combinations thereof.

3. A method as in claim 1 wherein the copper-zinc carboxylic acid salt having copper and zinc cations in the same molecule is a copper-zinc malonate.

4. A method as in claim 3 wherein the copper-zinc malonate comprises about 16.5% copper and about 12.4% zinc.

5. The method of claim 1 wherein the molar ratio of copper to zinc in the copper-zinc carboxylic acid salt having copper and zinc cations in the same molecule is from about 1:1 to about 3:1.

6. The method of claim 1 wherein the molar ratio of copper to zinc in the copper-zinc carboxylic acid salt having copper and zinc cations in the same molecule is from about 1:1 to about 2:1.

7. The method of claim 1 wherein the copper-zinc carboxylic acid salt having copper and zinc cations in the same molecule is present in an amount from about 0.001 to about 5% by weight of the composition.

8. The method of claim 1 wherein the copper-zinc carboxylic acid salt having copper and zinc cations in the same molecule is present in an amount from about 0.05 to about 1% by weight of the composition.

9. The method of claim 1 wherein the copper-zinc carboxylic acid salt having copper and zinc cations in the same molecule is present in an amount from about 0.1 to about 0.5% by weight of the composition.

10. A method as in claim 1 wherein the composition is a solution, emulsion, microemulsion, suspension, cream, lotion, gel, powder, solid composition, or combinations thereof.

11. The method according to claim 1, wherein the composition comprises a dermatologically acceptable carrier or diluent.

12. A method for forming collagen, elastic fibers, elastin, or tropoelastin in the skin of a patient comprising contacting an area of the skin in need thereof with an effective amount of a composition wherein the composition comprises one or more copper-zinc carboxylic acid salt having copper and zinc cations in the same molecule.

13. The method according to claim 12, wherein the composition comprises a dermatologically acceptable carrier or diluent.

14. The method according to claim 12, wherein the copper-zinc carboxylic acid salt having copper and zinc cations in the same molecule is selected from the group consisting of copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azelate, copper-zinc sebacate, copper-zinc dodecanoate, and combinations thereof.

15. The method according to claim 12, wherein the copper-zinc carboxylic acid salt having copper and zinc cations in the same molecule is a copper-zinc malonate.

16. The method according to claim 15, wherein the copper-zinc malonate comprises about 16.5% copper and about 12.4% zinc.

17. The method according to claim 12, comprising from about 0.001 to about 5 percent by weight of the copper-zinc carboxylic acid salt having copper and zinc cations in the same molecule.

18. The method according to claim 12, comprising from about 0.05 to about 1 percent by weight of the copper-zinc carboxylic acid salt having copper and zinc cations in the same molecule.

19. The method according to claim 12, comprising from about 0.1 to about 0.5% percent by weight of the copper-zinc carboxylic acid salt having copper and zinc cations in the same molecule.

20. The method of claim 12 wherein the composition further comprises an active drug substance.

21. The method of claim 12 wherein the composition further comprises an active cosmetic substance.

22. The method of claim 12 wherein the composition further comprises humectant, solvent, water, or combinations thereof.

23. The method of claim 12 wherein the composition is in the form of a liquid, cream, oil, gel, fluid cream, lotion, emulsion or microemulsion.

* * * * *